United States Patent [19]

Kurz

[11] 4,119,400
[45] Oct. 10, 1978

[54] INSTALLATION FOR DISINFECTING, BY THE ACTION OF FORMALDEHYDE

[75] Inventor: Maurice Kurz, Geneva, Switzerland

[73] Assignee: Societe DETEC S.A., Geneva, Switzerland

[21] Appl. No.: 767,992

[22] Filed: Feb. 11, 1977

[51] Int. Cl.² ............... A61L 3/02; A61L 3/00; A61L 13/02

[52] U.S. Cl. .................. 422/298; 422/305; 422/306; 422/24

[58] Field of Search ............... 21/DIG. 4, 58, 91–93, 21/110

[56] References Cited

U.S. PATENT DOCUMENTS

| 1,062,404 | 5/1913 | Kiefer | 21/58 |
|---|---|---|---|
| 1,837,264 | 12/1931 | Hackley | 21/58 |
| 3,068,064 | 12/1962 | McDonald | 21/DIG. 4 |
| 3,547,576 | 12/1970 | Sheikh | 21/58 |
| 3,703,353 | 11/1972 | Kusterer et al. | 21/110 |
| 3,796,541 | 3/1974 | Gentil | 21/110 |
| 3,806,318 | 4/1974 | Siard et al. | 21/53 |
| 3,816,074 | 7/1974 | Decupper | 21/74 R |
| 3,958,935 | 5/1976 | Kowol | 21/58 |

*Primary Examiner*—Morris O. Wolk
*Assistant Examiner*—Bradley Garris
*Attorney, Agent, or Firm*—Anthony DeLaurentis

[57] ABSTRACT

Apparatus for disinfecting medical apparatus, and especially artificial respirators, by the action of formaldehyde fumes subsequently neutralized by ammonia fumes, the apparatus being adapted to avoid the deposition of crystalline hexamethylene tetramine inside the respirator and comprising an enclosure for receiving the medical apparatus, a source of formaldehyde fumes likely to spread within the enclosure, and an auxiliary neutralization chamber communicating with the enclosure and provided with a source of ammonia; the volume of the neutralization chamber being such as to allow ammonia fumes to spread and to come into contact with formaldehyde fumes for a sufficient time to ensure neutralization.

4 Claims, 4 Drawing Figures

INSTALLATION FOR DISINFECTING, BY THE ACTION OF FORMALDEHYDE

The present invention relates to a process and an installation for disinfecting, by the action of formaldehyde, such items as for example medical apparatus which may be the seat of pathogenic germs and which therefore require regular disinfection.

The invention relates more especially to an installation for disinfecting medical apparatus, such as in particular an artificial respirator, by the action of formaldehyde.

When an artificial respiration or reanimation apparatus is subjected to disinfection by formaldehyde, the crystalline hexamethylenetetramine produced by ammonia neutralising the formaldehyde is deposited in the pipes of the apparatus and may hinder the later functioning thereof and impede the perfect regularity of the patient's breathing.

In addition, the hexamethylene-tetramine which is a mild antiseptic thus slightly toxic, may in the long run provoke pulmonary disorders as it is inhaled with the air from the respirator apparatus into the patient's lungs.

It is an object of the invention to remedy these various drawbacks and to provide an installation for disinfection by formaldehyde with subsequent neutralization by ammonia, whilst avoiding the above-mentioned disadvantages associated with the deposit of hexamethylene-tetramine crystals in the disinfected apparatus.

To this end, the invention relates to a process for disinfecting medical apparatus or the like, of the type in which formaldehyde fumes are emitted into the enclosure to be desinfected, wherein, at the end of the disinfection cycle, the formaldehyde fumes are evacuated from the enclosure by the injection into said enclosure of a stream of rinsing gas previously brought to such temperature conditions that the formaldehyde is removed from the enclosure to be disinfected without polymerization and without formation of a parasitic deposit of trioxymethylene.

The invention also relates to an installation for the disinfection of medical apparatus by the action of formaldehyde of the type constituted by an enclosure adapted to be hermetically closed after the apparatus to be disinfected has been placed therein, the enclosure comprising a source of formaldehyde fumes which may spread in said enclosure, installation wherein said enclosure comprises a source of rising gas which causes the formaldehyde fumes inside the enclosure to be evacuated therefrom and which rinse the atmosphere inside the enclosure.

According to another feature of the invention, the installation is preferably associated with an auxiliary chamber communicating with said enclosure and adapted to receive, at the end of the disinfection cycle, the formaldehyde fumes coming from the disinfecting enclosure, said auxiliary chamber comprising a source of ammonia fumes for neutralising the formaldehyde fumes.

The invention will be more readily understood from reading the following description given with reference to the accompanying drawings, in which.

Figure 1:
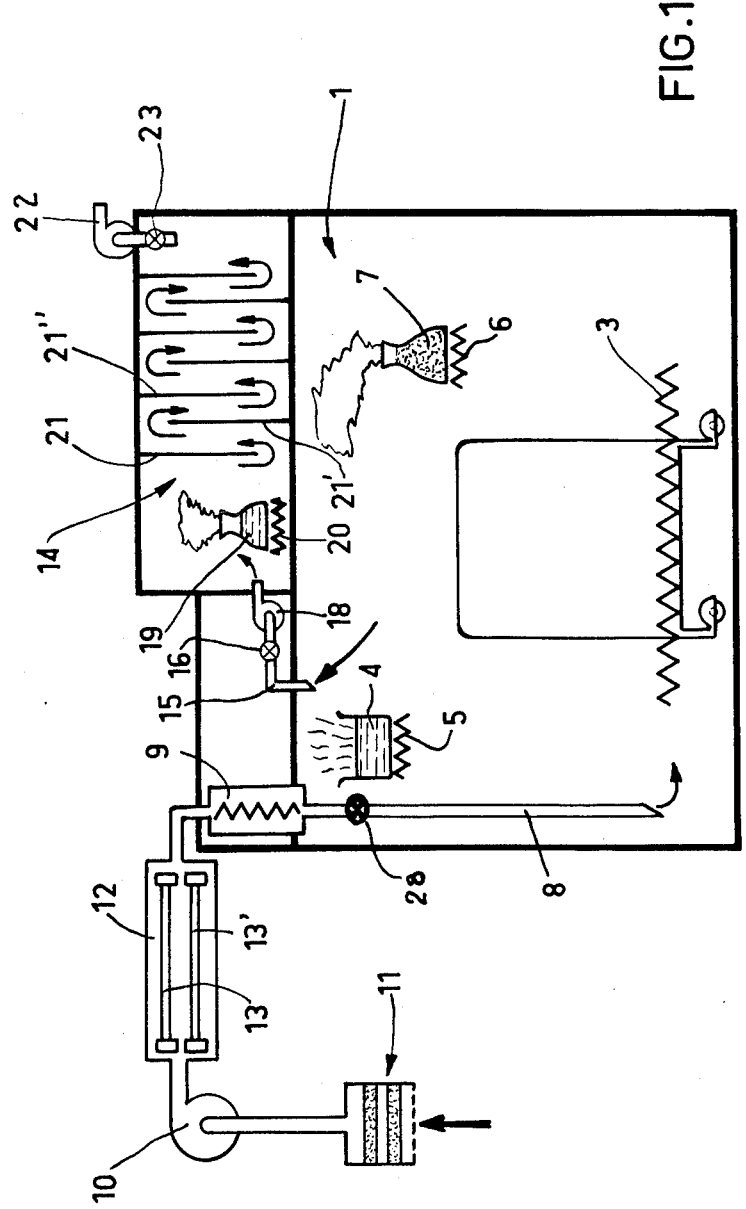
FIG. 1 shows a schematic view of the different functions of the apparatus.
Figure 2A:
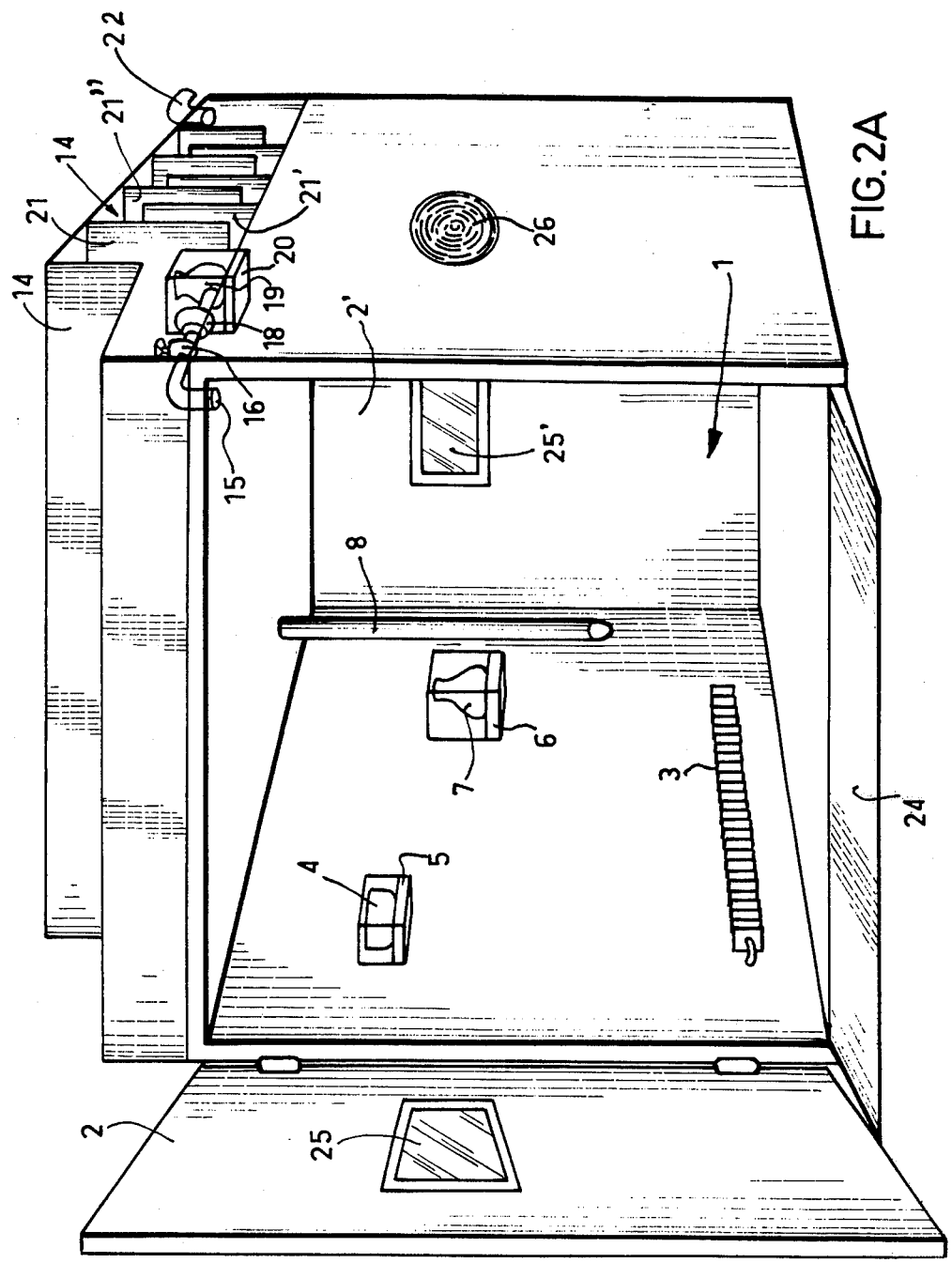
FIG. 2A shows a perspective view of a compartment made according to the invention, when open.

Referring now to the drawings, FIGS. 1 and 2 show an installation for disinfecting various items, particularly medical apparatus, composed of a compartment 1, generally parallelepipedic in form and defined by two side walls, a bottom or floor and a top or ceiling; two opposite hermetically sealable doors 2 and 2' constitute the entrance and exit respectively of the apparatus, thus allowing the contaminated apparatus to arrive from a soiled one and leave in an aseptic or clean one at the end of the disinfection cycle.

The apparatus to be disinfected will therefore be kept in the compartment 1 for the time necessary for the disinfectant to act.

The compartment is preheated, in known manner, by resistor 3; the actuation of said latter enables a temperature to be obtained of between 30° and 40° C. so as to bring the walls of the apparatus placed inside the compartment and subjected to disinfection to a temperature of about 35°, this being particularly suitable for an effective action of the formaldehyde without the formation of its trimer, trioxymethylene; if the temperature is too low the relative humidity is too low, said trioxymethylene may in fact be formed as crystals deposited on the walls of the apparatus to be disinfected; the polymeric form of the formaldehyde thus constituted would then be subjected to sublimation with subsequent emission of secondary or induced formaldehyde when the apparatus is used, and its toxic action would therefore be feared.

In order to obtain the desired relative humidity inside the compartment 1, a member for regulating the rate of humidity, e.g. in the form of a container 4 subjected to the action of a heater element 5, enables the desired relative humidity to be maintained in the compartment; the resistors 3 and 5 are subjected to a thermostatic regulation as will be described hereinbelow with reference to FIG. 3.

Inside the compartment 1, the formaldehyde is emitted by the action of the resistor 6 forming a heating plate and raising the temperature of the beaker 7 containing trioxymethylene, i.e. the trimeric form of formaldehyde which emits monomeric formaldehyde when sublimating by rise in temperature.

A pipe 8 is provided for blowing air into the enclosure or compartment 1 and it injects air therein which is intended to ensure an excessive pressure inside the compartment at the end of the disinfection cycle.

To this end, when the action of the formaldehyde is prolonged during the programmed time which corresponds to the optimum conditions of disinfection of the apparatus placed in the compartment, the pressurised air is injected through the electrovalve 28; in order to avoid a drop in temperature within the compartment, which would risk the formation of the trimeric formaldehyde, the pipe 8 is associated with a resistor 9 which raises the temperature of the rinsing gas injected into the enclosure, raising it to a temperature close to 40°; this air comes from a turbine 10 and it is purified by passage over a filter 11, then decontaminated by passage in a compartment 12 with UV tubes 13, 13'.

The compartment or enclosure 1 is associated with a secondary chamber 14 which is advantageously located thereabove; to this end, a channel 15 opens into the chamber 14 which it places in communication with the compartment 1 with the interposition of an electrovalve 16, preferably associated with a non-return valve.

The excessive pressure provoked in the compartment 1 will allow the mixture of air and formaldehyde fumes contained therein to be driven towards chamber 14; however, a pump 18 of the vaccum pump type may also be provided in pipe 15, consequently enabling the fumes to be sucked from the compartment 1 into the neutralisation chamber 14.

The source of ammonia fumes is located near the opening of the passage 15 from the compartment 1 to the chamber 14. This is preferably a container, e.g. a beaker 19 containing an aqueous solution of ammonia and associated with heater element 20.

The ammonia fumes thus emitted will mix with the formaldehyde fumes leaving the compartment 1 and the reaction of neutralisation with the formation of hexamethylene-tetramine will thus occur in the neutralisation chamber 14; to multiply the contacts of the two reagents (formaldehyde and ammonia) and in order to reduce the speed of the gaseous stream by increasing the dwell time in the neutralisation chamber, baffles 21, 21', 21" are positioned in the chamber 14, thus obliging the gaseous stream to follow a zigzag path from the opening of the channel 15 guiding the formaldehyde fumes in the neutralisation chamber to the evacuation thereof towards the atmosphere through the outlet 22 provided with the electrovalve 23.

The doors 2 and 2' are obviously provided with gaskets to avoid any loss or leakage of formaldehyde from the inside of the compartment.

Ramps 24, 24' forming an inclined plane are associated with each door so to allow the apparatus to be disinfected to be easily rolled into the compartment.

Portholes 25, 25' disposed on the front and rear doors enable the interior of the compartment to be supervised from the outside, whilst a "glove" type device 26 also enables items inside the compartment to be handled from the outside.

A control board 26 enables the different successive phases of functioning of the apparatus to be displayed and controlled by pressing on the control buttons 27, 27',27", etc.

The apparatus to be disinfected, e.g. an artifical respirator, is introduced through door 2 into the interior of the compartment; the two doors 2 and 2' are closed and a cycle of heating and humdity regulation begins for a preregulated period so as to bring the interior of the compartment to the desired temperature and relative humidity; for example, a temperature of the order of 35° and relative humidity of the order of 75%, these conditions avoiding the formation of polymerised formaldehyde.

The functioning of the apparatus will be described hereinafter with reference to FIG. 3.

By acting on starter button M, the telebreaker A allows the general 20 amps switch F to function; this latter trigger the time-switch B of 45 minutes corresponding to the time for the heater element 3, the thermostat device associated therewith, as well as the humidity regulation assembly 4 and 5 to be switched on and opeate; at the end of the preparatory cycle of 45 minutes, the interior of the compartment and the apparatus subjected to disinfection which it contains, are brought to the optimum conditions of temperature and relative humidity, i.e. substantially 35° to 40° C. and 75% respectively.

At the end of the 45 minute preheating period, the time-switch B triggers a timed relay C of 3 seconds which will automatically stop the assembly at the end of the cycle. A contact of the relay C starts off the fast motor M1 which positions the cam 30; the cycle commences and the rest contact of the cam 31 triggers the heating of the resistor 6 causing the formaldehyde fumes to be emitted; to this end, the sublimation of the trioxymethylene contained in the beaker 7 provokes the emission of formaldehyde fumes (more stable than the formaldehyde is liquid solution ); the resistor 6 is a heater element of 300W thermostat 150° C. maximum, in order not to degrade the product.

After 20 minutes of sublimation, the formaldehyde fumes have developed in the compartment and the period of contact of the fumes in the disinfection enclosure, which has been previously selected on the keyboard by pressing one of keys; 3 hours, 6 hours or 9 hours, is started. Whatever the cycle chosen, operation is ensured by the slow motor M2.

At the end of the contact time, the cam 32 actuates its contact in position R, this having for its effect to apply a voltage of 220V on the 300 W heater element 20 which consequently heats the beaker 19 containing a solution of ammonia. The duration of evaporation of the ammonia is also 20 minutes. The emission of ammonia in the auxiliary neutralisation chamber 14 is effected by means of a pump 18 which is turned on for a duration varying from 30 minutes to one hour. At the same time, a first electrovalve 16 is actuated in order to suck the fumes contained in the compartment and which are constituted by hot, humid air containing formaldehyde fumes. The second electrovalve 23 will be actuated after an adjustable delay time (of the order of a few seconds) following the actuation of the electrovalve 16, in order thus to ensure the evacuation of the glass, i.e. the air containing hexamethylene-tetramine, resulting from the neutralisation of the formaldehyde by ammonia, to the outside, but after separation of the solid hexamethylene-tetramine.

At the end of the disinfection, neutralisation and rinsing cycle, the slow moteur M2, by the position of the cams, stops pump 18 (for delivering formaldehyde towards the neutralisation enclosure) and pump 10 (for injecting rinsing gas) with closure of the electrovalves 16, 28 and 23; the slow motor then continues to rotate in order to position the cams for a subsequent cycle and the timed relay E selects the stop of the cycle.

Figure 2B:
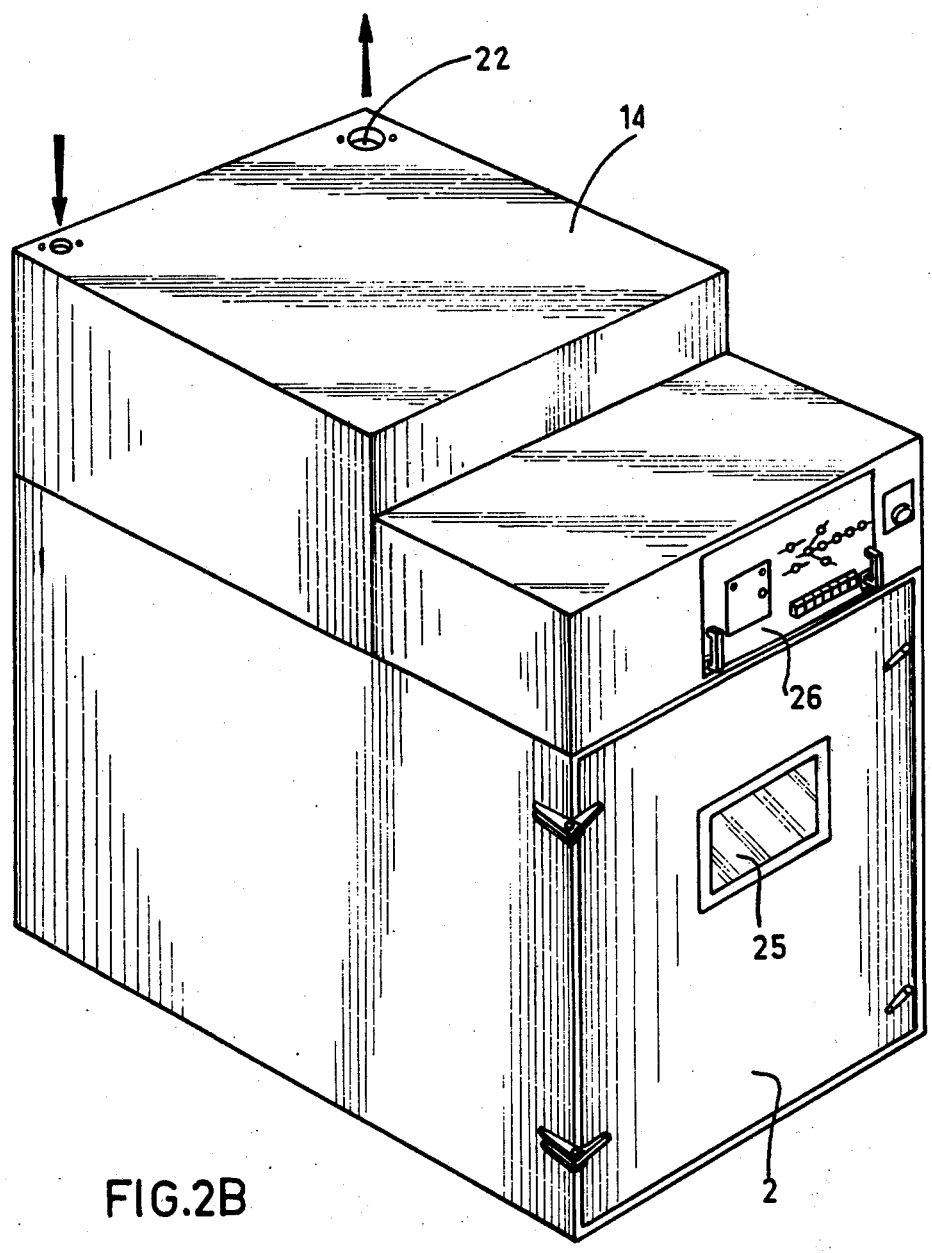
FIG. 2B shows the same compartment with the doors closed.
Figure 3:
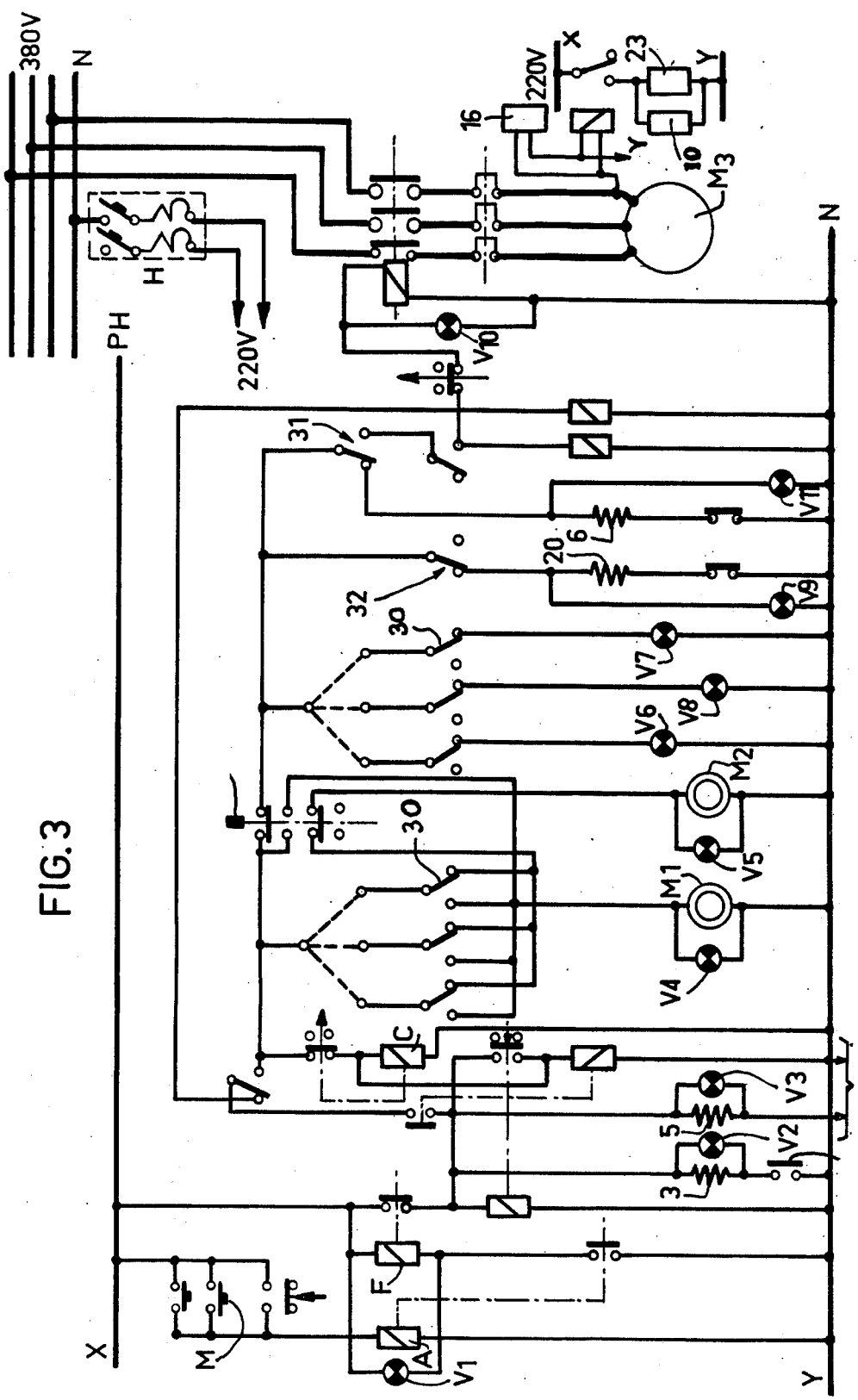
FIG. 3 shows the electrical diagram representing the various control and signalling elements of the various members of which the installation is composed.

Various warning lights enable the development of the cycle to be followed; as shown in the diagram of FIG. 3 and in FIG. 2B, the warning lights are as follows;

V 1 Start
V 2 Preheating
V 3 Hygrometric regulation
V 4 Fast motor (M1)
V 5 Slow motor (M2)
V 6 Formaldehyde cycle 9 hours (contact time of the formaldehyde fumes)
V 7 Formaldehyde cycle 3 hours (contact time of the formaldehyde fumes)
V 8 Formaldehyde cycle 6 hours (contact time of the formaldehyde fumes)
V 9 Emission of ammonia
V10 Delivery pump (either pump 18 or pump 10 or both)
V11 Emission of the formaldehyde.

The return to zero may be triggered off and the fast motor M1 may be started up again by disconnecting the slow motor M2; cams return to position at the end of the cycle.

It will be noted that upon each stop (voluntary or otherwise) such as for example due to a power cut, the heating and relative humidity regulating cycle is automatically re-established for its duration of 45 minutes as soon as the current returns. Under these circumstances, the cycle will continue from where it was cut, but after said preheating and relative humidity regulation period of 45 minutes; during this time, no return to zero can be effected.

In this way, the development of formaldehyde in the compartment under temperature conditions which would not be optimum and which would lead to the deposit of trioxymethylene crystals inside the apparatus to be disinfected, is avoided. The disinfection of the apparatus does not require any prior dismantling and thus avoids loss of time.

A female socket may be provided inside the compartment for connecting an electrically operated medical apparatus such as a respirator, thus enabling this apparatus to operate during the disinfection period in order to allow a circulation of the formaldehyde fumes inside said apparatus.

What is claimed is:

1. Apparatus for disinfecting medical apparatus and especially artificial respirators by the action of formaldehyde fumes subsequently neutralized by ammonia fumes and adapted to avoid the deposit of crystalline hexamethylene tetramine inside the medical apparatus, said disinfecting apparatus comprising:

a disinfection enclosure adapted to receive a medical apparatus and provided with at least one hermetically closed door through which the medical apparatus is inserted and subsequently removed;

means for introducing formaldehyde fumes into said enclosure;

air inlet means for introducing air into said enclosure;

a source of heat for raising the temperature of the air to a predetermined value;

a decontamination compartment having a UV source for decontaminating the air introduced into said enclosure;

pump means for conveying the air from outside of said enclosure successively to said decontamination compartment to said source of heat and to said disinfecting enclosure;

an auxiliary neutralization chamber communicating with said disinfecting enclosure and provided with a souce of ammonia fumes, the volume of said neutralization chamber being such as to allow said ammonia fumes to spread and to come into contact with formaldehyde fumes for a sufficient time to ensure neutralization thereof;

pump means connected to said disinfection enclosure and to said neutralization chamber and adapted to withdraw the formaldehyde fumes from said disinfection enclosure and deliver them to said neutralization chamber; and a non-return valve allowing the formaldehyde fumes to be conveyed to said neutralization chamber and precluding the reverse movement thereof from said neutralization chamber to said disinfection enclosure.

2. The appartus of claim 1 wherein said air inlet means is provided with an electrovalve.

3. The apparatus of claim 1, wherein said neutralization chamber comprises baffles adapted to slow down and extend the path of the ammonia fumes and the formaldehyde fumes in said neutralization chamber by multiplying the contacts between the ammonia and formaldehyde and by ensuring a complete neutralization of the formaldehyde by the ammonia.

4. The apparatus of claim 1, wherein said disinfection enclosure comprises female socket means inside said enclosure and adapted to connect the medical apparatus so as to allow electrical actuation thereof and circulation of formaldehyde fumes inside said medical apparatus.

* * * * *